United States Patent
Moyers et al.

(10) Patent No.: US 9,765,084 B2
(45) Date of Patent: Sep. 19, 2017

(54) RECOVERY AND REFINING OF DIANHYDROSUGARS

(75) Inventors: Charles Guthrie Moyers, Charleston, WV (US); James Kermit Withrow, Charleston, WV (US); John Leonard Stephens, Hurricane, WV (US)

(73) Assignee: Iowa Corn Promotion Board, Johnston, IA (US)

( * ) Notice: Subject to any disclaimer, the term of this patent is extended or adjusted under 35 U.S.C. 154(b) by 0 days.

(21) Appl. No.: 12/421,245

(22) Filed: Apr. 9, 2009

(65) Prior Publication Data

US 2009/0259056 A1 Oct. 15, 2009

Related U.S. Application Data

(60) Provisional application No. 61/043,943, filed on Apr. 10, 2008.

(51) Int. Cl.
| | |
|---|---|
| *A61K 31/495* | (2006.01) |
| *A61K 31/7048* | (2006.01) |
| *A61K 9/28* | (2006.01) |
| *A61K 9/48* | (2006.01) |
| *C07D 493/04* | (2006.01) |
| *C07H 1/06* | (2006.01) |

(52) U.S. Cl.
CPC ............ *C07D 493/04* (2013.01); *C07H 1/06* (2013.01)

(58) Field of Classification Search
USPC .......................................... 549/464; 536/124
See application file for complete search history.

(56) References Cited

U.S. PATENT DOCUMENTS

| | | | |
|---|---|---|---|
| 3,454,603 | A | 7/1969 | Hartman |
| 4,313,884 | A | 2/1982 | Arena |
| 4,408,061 | A | 10/1983 | Salzburg et al. |
| 4,564,692 | A * | 1/1986 | Feldmann et al. ............ 549/464 |
| 4,659,846 | A | 4/1987 | Maurer et al. |
| 4,861,513 | A | 8/1989 | Lueders et al. |
| 6,407,266 | B2 | 6/2002 | Bhatia |
| 6,639,067 | B1 | 10/2003 | Brinegar et al. |
| 6,670,033 | B1 | 12/2003 | Hubbard et al. |
| 6,818,781 | B2 | 11/2004 | Bhatia |
| 6,831,181 | B2 | 12/2004 | Bhatia |
| 6,849,748 | B2 | 2/2005 | Moore et al. |
| 6,864,378 | B2 * | 3/2005 | Bhatia ........................... 549/464 |
| 7,122,661 | B2 | 10/2006 | Fleche et al. |
| 7,420,067 | B2 | 9/2008 | Sanborn |
| 2002/0028959 | A1 | 3/2002 | Andrews et al. |
| 2004/0013217 | A1 | 1/2004 | Dietrich et al. |
| 2004/0030161 | A1 | 2/2004 | Bhatia |
| 2004/0110969 | A1 | 6/2004 | Fleche et al. |
| 2007/0173652 | A1 | 7/2007 | Holladay et al. |

FOREIGN PATENT DOCUMENTS

| | | |
|---|---|---|
| WO | 9627029 | 9/1996 |
| WO | 00/14081 A1 | 3/2000 |

OTHER PUBLICATIONS

Ault, A. Techniques and Experiments for Organic Chemistry, 1987, pp. 44-48.*
Ault , Techniques and Experiments for Organic Chemistry, 1987, pp. 44-48.*
Barker, Robert, Conversion of Acyclic Carbohydrates into Tetrahydrofuran Derivatives. Acid-Catalyzed Dehydration of Hexitols, J. Org. Chem., Feb. 1970, vol. 35, No. 2, pp. 461-464.
Hockett, et al., Hexitol Anhydrides. The Structures of the Anhydromannitols of Brigl and Gruner. The Structure of Isomannide, Am. Chem. So. Jun. 1946, vol. 68., pp. 930-935.
Soltzberg, et al., Hexitol Anhydrides. Synthesis and Structure of Arlitan, the 1, 4-Monoanhydride of Sorbitol, J. Am. Chem. Soc., Jun. 18, 1946, vol. 68, No. 6, pp. 919-921.
Fleche, et al., Isosorbide Preparation, Properties and Chemistry, Starch/Starke, 1986, vol. 38(c), pp. 26-30.
Goodwin, et al., Preparation of bicyclic hexitol anhydrides by using acidic cation-exchange resin in a binary solvent 13 C-N.m.r. spectroscopy confirms configurational inversion in chloride displacement of methanesulfonate in isomannide and isosorbide derivatives, Carbohdrate Res., 1980, vol. 79, pp. 133-141.
Van Hook, Andrew, Crystallization, Theory and Practice, Reinhold Publishing Corporation, 1961, p. 251.
Randolf, Alan D. and Larson, Maurice A., Theory and Particulate Processes, Academic Press, 1988, pp. 122-123.

* cited by examiner

*Primary Examiner* — Ganapathy Krishnan
(74) *Attorney, Agent, or Firm* — Davis, Brown, Koehn, Shors & Roberts, P.C.; Kent A. Herink; Matthew W. Coryell

(57) ABSTRACT

A process for the production of a refined dianhydrosugar-containing product is disclosed. The process includes controlled continuous crystallization of the dianhydrosugar-containing product to produce a solution saturated with the dianhydrosugar. The saturated solution is mechanically separated, for example by centrifugation, and the crystalline product is washed. The only solvent used is water. The dianhydrosugar-containing product is upgraded to at least 99.8% purity and recovery is 95% or greater.
Recrystallization of the dianhydrosugar of 99.8% purity results in an ultra pure product containing at least 99.99% dianhydrosugar.

8 Claims, 2 Drawing Sheets

RECOVERY AND REFINING OF DIANHYDROSUGARS

This application claims priority to U.S. Patent Application Ser. No. 61/043,943, filed Apr. 10, 2008.

GOVERNMENT SUPPORT

This invention was made with government support under Grant Number: 2009-10002-05143 awarded by the National Institute of Food and Agriculture within the U.S. Department of Agriculture and the. Accordingly, the government has certain rights in this invention.

BACKGROUND OF THE INVENTION

The invention relates generally to methods of recovering and refining dianhydrosugars and, more specifically, to methods for batch, semi-batch and continuous recovery and purification of isosorbide.

The 1,4:3,6-dianhydrosugars, of which isosorbide is an example, are derived from natural products. Therefore, these compounds are classified as "renewable resources." Furthermore, 1,4:3,6-dianhydrosugars, such as isosorbide, can be used as starting materials and intermediates in chemical reactions. For example, isosorbide is reported to be useful in the production of pharmaceutical compounds, plastic and polymer production, and in other commercial uses such as in the production of polyurethanes, polycarbonates, and polyesters.

For isosorbide to be used as a monomer in high volume polymers and copolymers, for applications such as containers, it needs to be produced in large quantities, preferably in a continuous process and with low operating costs.

A new process for producing isosorbide from sorbitol without the use of a vacuum to remove water formed during the reaction has been developed and is the subject of a co-pending patent application. The temperature and acid strength of the reaction mixture are adjusted to control the amount of water in the reaction mixture to provide conditions for high selectivity and productivity of isosorbide. Crude isosorbide is removed from the reaction mixture via low pressure evaporation and is condensed to produce a concentrated isosorbide solution containing small quantities of high boiling impurities. Typically the quality of crude isosorbide in the evaporator condensate from the enhanced reaction process is in the 97-98 weight percent range (on a water free basis).

U.S. Pat. No. 4,564,692 describes techniques for crystallizing isosorbide and other anhydrosugar alcohols from concentrated aqueous solutions by controlled cooling crystallization from seeded solutions. Unlike the techniques described in this specification, supersaturation was maintained in the range where existing crystals continued to grow without primary or secondary nucleation providing new seed crystals.

U.S. Pat. No. 6,670,033 describes laboratory procedures for purification of anhydrosugar alcohols, including isosorbide. Preferably, the purification is by distillation followed by recrystallization from methanol, ethanol, or ethylene glycol. Employment of water as a solvent was not addressed in this patent.

U.S. patent application Ser. No. 10/414,606 concerns a continuous process for recovering and purifying isosorbide from a water vapor stream. The process is speculative and unproven and no data are presented in the application.

U.S. Pat. No. 7,122,661 describes a sequential treatment technique for trace impurity removal from previously crystallized isosorbide (from organic solvent) involving dissolution in water and treatment with decolorizing carbons and ion exchange resin. The final product from this treatment is a purified isosorbide/water solution. Water is evaporated and the concentrated isosorbide melt is solidified and crushed to produce particulate material.

SUMMARY OF THE INVENTION

In this invention, "crude" isosorbide is upgraded to at least 99.8% (refined product) and optionally to 99.99% purity (ultra-refined product) by a sequence of controlled batch, semi-batch or continuous crystallization, centrifugal filtration of the isosorbide crystals from the saturated solution, purified water washing of the crystalline product and low temperature vacuum drying of the product. The solvent of choice for crystallization is purified water. No organic solvents are used anywhere in this process. Crystallization of isosorbide from solution is achieved by indirect cooling of the isosorbide solution.

Maximum recovery of isosorbide from the reactor solution is important to achieve economics of large-scale operation. FIG. 1 is a schematic of the continuous process which includes the separation elements necessary to both produce refined and/or ultra-refined isosorbide product and the separation elements necessary to extract and recycle isosorbide from the various process streams. In the continuous embodiment of this invention, greater than 99.8% purity crystalline isosorbide (refined product) is obtained from the initial stage of crystallization (CRY1). The crystallization vessel is maintained at 20° C. Crystalline isosorbide is removed by mechanical separation (CENT1) and dried (DRY1). The isosorbide depleted effluent liquor from CENT1 is directed to evaporator (EVAP1) for water removal and from there to evaporator (EVAP2) where 98-99 weight percent isosorbide is removed overhead and recycled to the crystallizer. A small "heavies" purge is removed from the evaporator kettle. Overall recovery of isosorbide based on crude reactor feed is 97-98%.

An ultra-refined isosorbide product may be obtained by dissolving the undried isosorbide from CENT1 in purified water and using the identical processing protocol as CRY1. The quality of the ultra-refined isosorbide is at least 99.99% (water free basis).

A purpose of the invention is to provide a fast and productive method for the recovery and refining of dianhydrohexitols, and particularly isosorbide.

Another purpose of the invention is to provide a batch, semi-batch or continuous process for refining and purifying dianhydrosugars using purified water as a solvent.

These and other objects of the invention will be understood by those of skill in the art upon a review of this specification.

DESCRIPTION OF THE INVENTION

Each step in the transformation of sorbitol to mannitan (and iditan) or sorbitan, and the conversion of sorbitan to isosorbide, produces an equivalent of water. The reaction scheme is reproduced below (Scheme 1).

Large easily separable high purity crystals of isosorbide are produced using this technique.

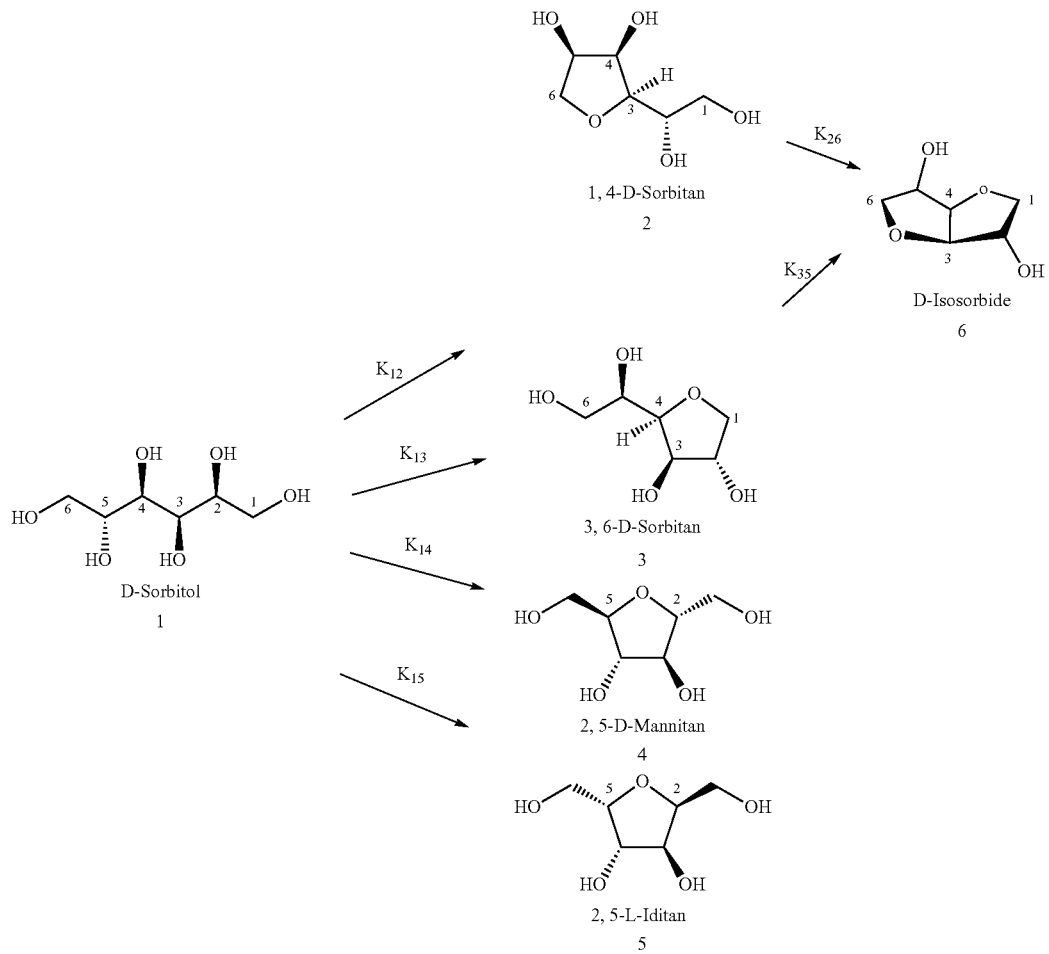

The present invention provides an improved process for the refining and purification of a dianhydrosugar such as those derived from a sugar alcohol via the intermediacy of the sugar alcohol anhydride. Suitable sugar alcohols include iditol, mannitol and sorbitol; consequently suitable dianhydrosugars include isoidide, isomannide and isosorbide.

Crystallization is a two step process, nucleation and growth. Nuclei are normally created by primary and secondary phenomena. Primary nucleation is initiated by supersaturating the solution until spontaneous nucleation occurs. Secondary nucleation occurs when nuclei spawn from existing crystals. For many systems primary nucleation occurs only with very high supersaturations and/or mechanical or electrical external stimulus. In these cases inoculating or seeding of the supersaturated solution with like crystals is often employed. Isosorbide/water solutions normally require seeding to initiate the crystallization process. All of the published patents that contain experimental data use seeding to recover the dissolved isosorbide from solution. In this invention secondary nucleation has been discovered, surprisingly, to be an effective mechanism for creating sufficient nuclei to sustain semi-batch or continuous operation and departs from the typical batch crystallization techniques.

EXAMPLE 1

Batch Processing

Crude isosorbide from the Enhanced Reaction Process normally contains 97-98 weight percent isosorbide (water free basis). It has been discovered that high purity isosorbide can be recovered from crude material by careful manipulation of the water content, seeding technique, cooling rate, residence time and final batch temperature.

Figure 1:
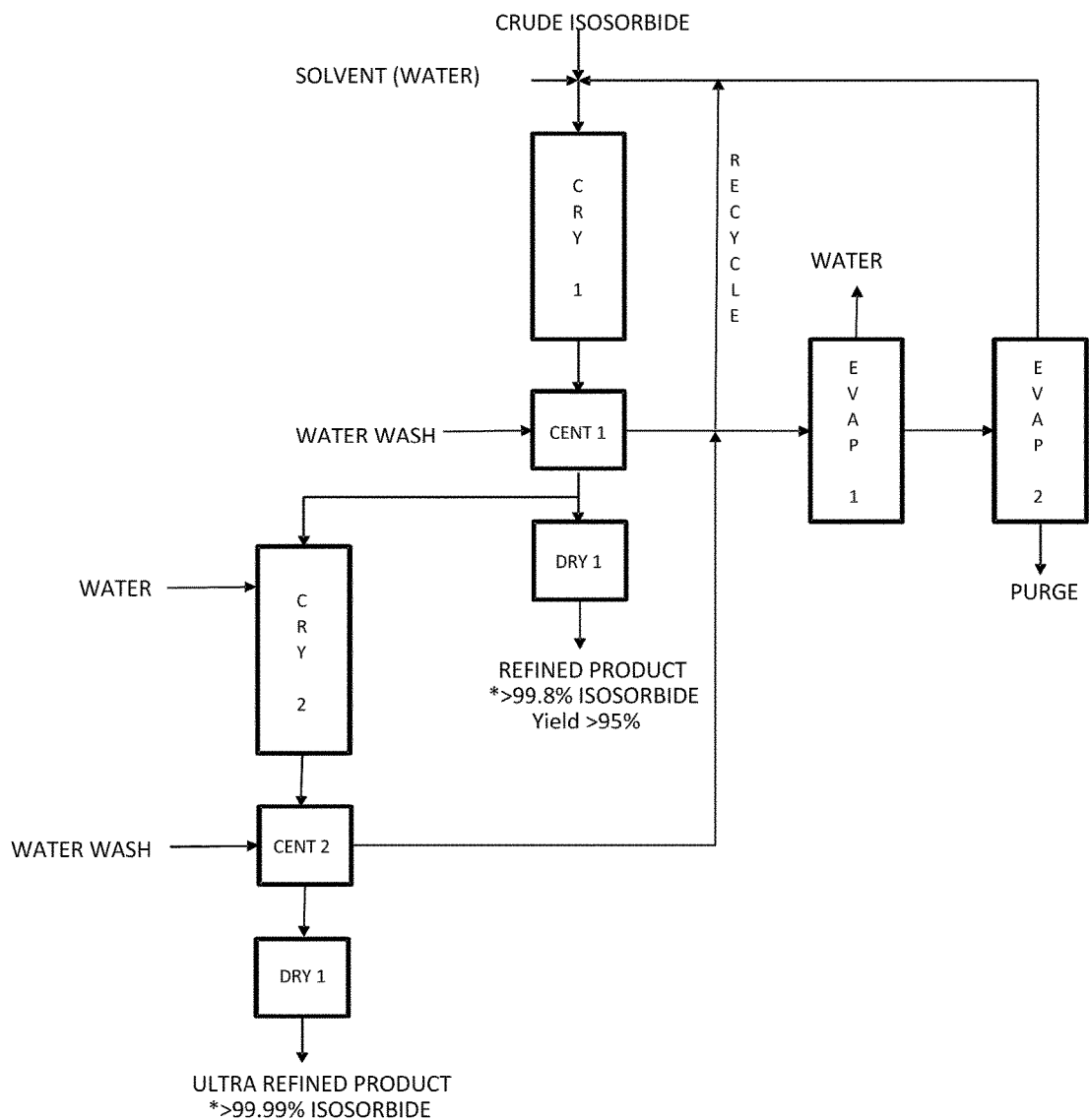
FIG. 1 is a schematic diagram of a continuous process of the present invention.
Figure 2:
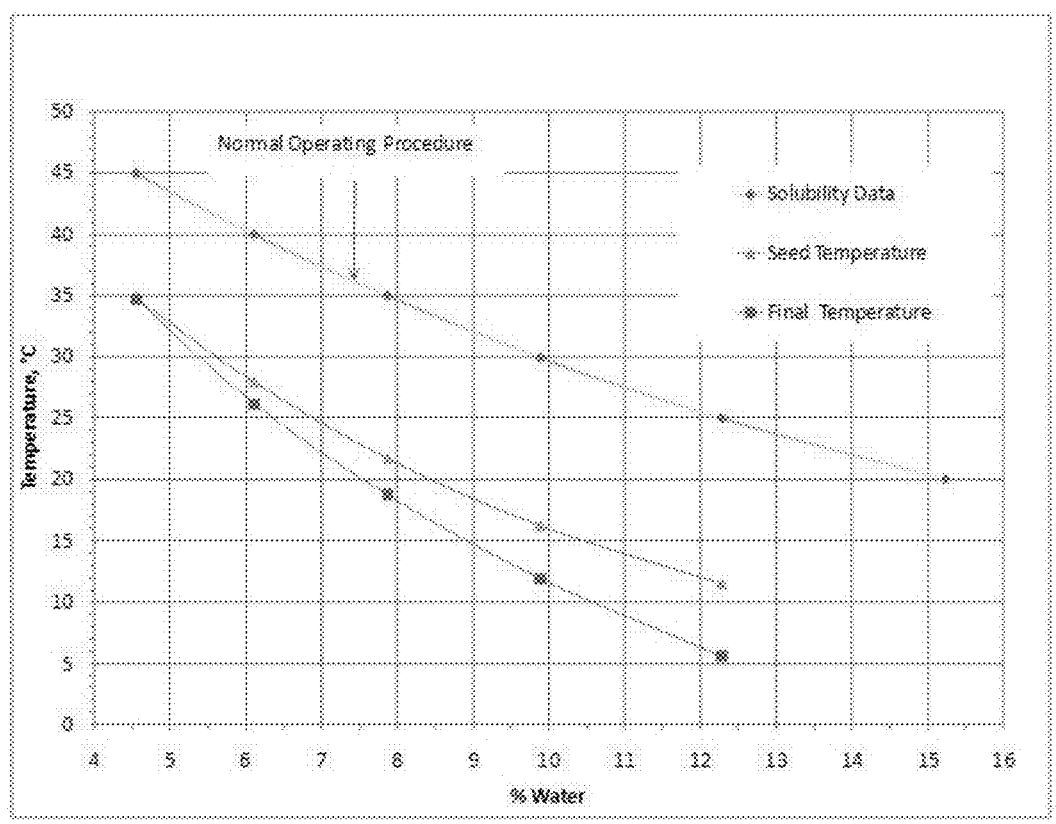
FIG. 2 is a batch crystallization operating chart.

Description of Batch Crystallization: FIG. 2 contains the solubility characteristics of isosorbide in water, the typical batch seeding temperature and the final crystallization temperature. Crude isosorbide liquid from the Enhanced Reaction Process is adjusted to 6-10 weight percent water, preferably 8 percent, and then added to a 15 liter jacketed vessel with 10-12 liters of operating volume and indirectly cooled to 24° C. while mechanically stirring. The mixture is then seeded with 0.1 weight percent isosorbide crystals (based on total charge weight). The mixture is then slowly cooled to 20° C. The resultant isosorbide/water slurry is separated in a variable speed centrifugal filter and the crystal cake washed with 0.05 grams of wash per gram of isosorbide crystals. Total batch time is normally 4 to 6 hours, preferably about 4 hours. Product purity is greater than 99.8% and recovery (based on isosorbide contained in crude feed) is about 35%.

In a run of the batch process, 18,900 grams of crude isosorbide which contained 8% by weight of water was placed into a crystallizer equipped with a rotating agitator and jacket for heating and cooling. The mixture was placed in the crystallizer at a temperature of 44° C. and cooled to 20° C., at which time it was seeded (inoculated) with 65 grams of isosorbide crystals. The resulting slurry of solids and liquid was then gradually cooled to 17° C. over a period of 2.5 hours. The crystals were separated from the mother liquor by centrifuging and purified by washing with cold water at a ratio of 0.05 gm water/gm isosorbide. The yield of isosorbide was 4760 grams, a recovery of 32% based on the initial amount of isosorbide in the crude material. The recovered isosorbide had a purity (GC) of greater than 99.8% and a water content of less than 1.5%. The product was then dried to <0.25% water in a batch vacuum dryer.

EXAMPLE 2

Semi-Batch Processing

Up to half of the volume of an existing crystallizer charge can be processed and then replenished with fresh crude feed solution. This new mixture can be successfully crystallized by maintaining the final batch temperature at previous condition for 2-4 hours. No additional seeding is required. In effect the new mixture is self-seeded from the crystals remaining from the previous crystallization. This semi-batch procedure can be repeated as often as desired.

The batch crystallization illustration described previously was repeated except that 15800 grams of crude isosorbide were placed in the crystallizer at an initial temperature of 40° C. The heavy liquor, which contained 8% by weight water, was then cooled to 18° C. and seeded with 45 grams of isosorbide crystals. The mixture was then cooled to 20° C. over a period of 2 hours. Crystals from approximately one-half of the slurry mixture were recovered as described in Example 1 and washed with cold purified water with a ratio of 0.05 gm water/gm isosorbide. The yield of isosorbide crystals from this half batch was 2060 grams.

Crude isosorbide and purified water were added to the remaining mixture in the crystallizer to give a total of 14,500 grams containing 8% by weight water. The slurry of isosorbide and water was cooled from 32° C. to 19° C. without seeding over a period of 2.5 hours. The crystals were recovered as in Example 1 and washed with cold distilled water at a ratio of 0.05 gm water/gm isosorbide. The total yield of isosorbide from both batches was 5190 grams, a recovery of 22%. The recovered isosorbide crystals had purity (GC) of greater than 99.8% (water free basis) and a water content of less than 1.5%. The isosorbide crystals were dried to 0.25% water in a batch vacuum dryer operating at low vacuum.

EXAMPLE 3

Continuous Processing

Continuous crystallization of crude isosorbide from a water solvent has been demonstrated in a pilot crystallization system. The major equipment consists of a heated feed tank and regulated feed pump, an agitated 15 liter working volume jacketed crystallizer; an external tubular heat exchanger, circulation pump, and a high speed centrifugal filter with provision for washing the recovered isosorbide cake. Product from the centrifuge is dried in a batch vacuum tumble dryer.

Before initiating continuous operation the crystallizer is charged with suitable feed solution and the batch crystallization procedure is used to develop a slurry of crystals. Crude isosorbide containing 97-98% by weight isosorbide is added to the heated feed tank. Distilled water is added to the feed tank to provide a solution containing from 6-10% water, preferably 8%. The contents of the crystallizer are cooled to 18-22° C., preferably 20° C. and isosorbide seeds are introduced. The quantity of seed required is small. Typically 0.1 weight percent of the total quantity of solution in the crystallizer vessel provides sufficient seed. After seeding and dissipating the heat of crystallization (crystallization is exothermic) the slurry is slowly cooled to 18-20° C.

After the slurry of isosorbide crystals is established and the crystallizer temperature equilibrated at, for example, 18° C., continuous feed is initiated from the feed tank. Feed tank temperature is maintained 5-10° C. above the saturation temperature of the feed solution. For example a feed solution containing 8% water which has a saturation temperature of 35° C. the feed tank temperature will be maintained at 40-45° C. Feed rate is initiated at 2000 ml per hour and gradually increased to 7500 ml per hour. This roughly corresponds to a residence time (crystallizer volume/volumetric feed rate) of 7.5 to 2 hours. As the feed rate increases the need for additional heat transfer is provided by an external cooling cycle. Slurry is removed from the crystallizer vessel and pumped through a cooler and returned into the crystallizer. Periodically crystal slurry is pumped from the crystallizer vessel into a batch automatic centrifugal filter where the mother liquor and the crystals are separated. Isosorbide crystals are retained on the inside of the spinning basket by a restraining screen and the mother liquor solution forced through the screen into the centrifuge discharge shroud, thus effectively separating the product isosorbide solids and associated liquid. The isosorbide crystals are washed with a small quantity of cold distilled water to displace impure mother liquor and remove color. The quantity of wash water is normally 0.05 gm of water wash per gm of dry isosorbide cake. Product is dried at low temperature (<50° C.) in a vacuum batch dryer to 0.25 weight percent or less.

Product purity of greater than 99.8% isosorbide is achieved via the above procedure. Isosorbide recovery is typically 30 percent of the isosorbide entering the crystallizer. For a commercial system overall recovery of isosorbide can be maximized to near 100% by recycling centrate and/or removing centrate to an evaporator where the isosorbide is removed, condensed and recycled to the crystallizer.

In a specific example, fifteen liters of crude isosorbide solution containing 97.5 percent by weight isosorbide were introduced to an agitated laboratory jacketed crystallizer, the water concentration was adjusted to 8 weight percent, and the contents were cooled without seeding to 20° C. The solution self nucleated during the cooling and did not require seeding. After the system equilibrated, crude isosorbide solution, containing 8 weight percent water, and from 96.2-97.4 percent isosorbide on a water free basis was continuously pumped at the rate of 2000 ml per hour from a heated feed tank directly into the well-mixed crystallizer. At one hour intervals 2000 ml of crystallizer slurry were discharged and processed in a variable speed centrifugal filter. Isosorbide crystals retained inside the centrifuge screen bowl were washed with 0.05 grams of cold distilled water per gram of cake. Typically 525-765 grams of washed isosorbide crystals were obtained per 2000 ml charge to the centrifuge. Product purity ranged from 99.8 to 99.9 weight percent isosorbide on a water free basis. Moisture content varied from 0.44 to 0.55 weight percent. Continuous feeding was maintained for eight hours without interruption.

EXAMPLE 4

Production of Ultra-purity Product

Ultra-purity product is produced by water recrystallization of wet centrifuge product produced by any of the crystallization modes described previously. Purification procedures are identical. The difference is the source and purity of the initial starting material. From starting material containing 99.8% isosorbide, crystal product of greater than 99.99% is typically produced. Specific example of batch crystallization: Nineteen kg of 99.7% isosorbide are processed by adding distilled water to form a 6.8% aqueous solution, then cooling the isosorbide solution to 27° C. before adding 41 grams of seed crystals. The crystallizer contents are slowly cooled to 25° C. and retained at that temperature for 2 hours. The isosorbide crystalline slurry was then centrifuged in two parts. Each half was washed with 118 g cold (8-10° C.) distilled water. The first increment contained 2424 grams of wet isosorbide containing 0.75% water while the final increment contained 2327 grams of wet isosorbide containing 0.58% water. The isosorbide crystals were dried at low vacuum and 50° C. temperature using a batch vacuum rotating cone dryer and assayed at >99.99% isosorbide.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A process for the production of a refined dianhydrosugar-containing crystalline product, wherein the dianhydrosugar is selected from the group consisting of isoidide, isomannide and isosorbide, comprising the steps of:
    (a) producing a crude dianhydrosugar-containing mixture in water;
    (b) cooling the crude dianhydrosugar-containing mixture to saturation in a continuous reaction vessel;
    (c) seeding the crude dianhydrosugar-containing mixture with crystals of the dianhydrosugar;
    (d) agitating and cooling the crude dianhydrosugar-containing mixture to below 45 degrees C. to induce spontaneous formation of new dianhydrosugar seed crystals to create a crystal-containing slurry of mother liquor and crystals of the dianhydrosugar;
    (e) withdrawing a portion of the crystal-containing slurry from the vessel;
    (f) mechanical separation of the crystals of the dianhydrosugar from the crystal-containing slurry to produce a dianhydrosugar crystalline product;
    (g) lowering the water content of the mother liquor; and
    (h) returning the mother liquor to the continuous reaction vessel without the addition of new seed crystals.

2. The process as defined in claim 1, further comprising a solvent in the dianhydrosugar-containing product and wherein the solvent is used in a washing step.

3. The process of claim 2, wherein the solvent is purified water.

4. The process of claim 1, wherein the product purity of the crystalline product is greater than 99.8 weight percent dianhydrosugar.

5. The process of claim 4, wherein recrystallization of the crystalline product provides dianhydrosugar purity of greater than 99.99 weight percent.

6. The process of claim 1, wherein the overall recovery of the dianhydrosugar is greater than 95 percent.

7. The process of claim 1, wherein the mechanical separation step is selected from the group consisting of centrifugation and filtration.

8. The process of claim 1, further comprising the step of washing the mechanically separated crystals of the dianhydrosugar.

* * * * *